US005936728A

United States Patent [19]
Bouzid

[11] Patent Number: 5,936,728
[45] Date of Patent: Aug. 10, 1999

[54] FLASH PHOTOLYSIS METHOD AND APPARATUS

[75] Inventor: Ahmed Bouzid, Madison, Wis.

[73] Assignee: Noran Instruments, Inc., Middleton, Wis.

[21] Appl. No.: 09/060,008

[22] Filed: Apr. 14, 1998

[51] Int. Cl.[6] .................................................. G01N 21/63
[52] U.S. Cl. ........................................................ 356/318
[58] Field of Search ..................................... 356/317, 318, 356/417; 250/458.1, 459.1, 461.1, 461.2

[56] References Cited

U.S. PATENT DOCUMENTS

| 3,811,777 | 5/1974 | Chance . |
| 4,023,905 | 5/1977 | Chance . |
| 4,863,226 | 9/1989 | Houpt et al. . |

FOREIGN PATENT DOCUMENTS

| 4-336516 | 11/1992 | Japan | 356/317 |
| 6-160724 | 6/1994 | Japan | 356/317 |

OTHER PUBLICATIONS

Samuel S.H. Wang, et al., "Confocal Imaging and Local Photolysis of Caged Compounds: Dual Probes of Synaptic Function," Neuron, vol. 15, Oct. 1995, pp. 755–760.

Primary Examiner—F. L. Evans
Attorney, Agent, or Firm—Foley & Lardner

[57] ABSTRACT

Flash photolysis is carried out in a microscope imaging system while maintaining continuous and superimposed imaging of the target area to which the flash is directed as well as its surroundings. In scanning imaging systems an excitation optical coupler receives the flash excitation beam and directs it onto an optical path through an aperture spatial filter to a main optical coupler, which directs the excitation beam into the microscope. The scanning beam from the scanning system is also passed through the main optical coupler to the microscope and the reflected light from the specimen is passed back from the microscope through the main optical coupler to the scanning system in a normal fashion to allow imaging of the specimen when the excitation beam is not provided. The position of the excitation beam is determined by directing a portion of the scanning beam toward the same aperture through which the excitation beam passes and detecting when the scanning beam light passes through the aperture, which corresponds to the point in time at which the scanning beam is at the position on the specimen at which the excitation beam will be incident. The detected signal can then be correlated with the displayed image of the specimen to indicate the target position in the image. In full image capture systems which do not use scanning, a target illumination beam can be passed onto the same optical path on which the excitation beam will be directed to the microscope.

37 Claims, 4 Drawing Sheets

FLASH PHOTOLYSIS METHOD AND APPARATUS

FIELD OF THE INVENTION

This invention pertains generally to the field of biology and microscopy and particularly to microscopic imaging of flash-photolysized compounds in specimens.

BACKGROUND OF THE INVENTION

Flash photolysis is a technique utilized to study oxidation-reduction reactions in tissues, based on the fluorescence characteristics exhibited by the compounds in the specimen under study. In this technique a short pulse or flash of light is focussed onto a position in a sample; oxidation inhibited compounds are photolysized by the flash of light and are oxidized with a concurrent fluorescence emission. Photoactivatable caged compounds that are biologically inactive until exposed to ultraviolet (UV) light can be activated by flash photolysis. Flash photolysis techniques can be utilized in confocal laser scanning microscopes to provide both imaging and local photolysis of caged compounds. See Samuel S. H. Wang, George J. Augustine, "Confocal Imaging and Local Photolysis of Caged Compounds: Dual Probes of Synaptic Function," Neuron, Vol. 15, October, 1995, pp. 755–760. The confocal epifluorescence microscope can then be utilized to provide an image of the fluorescence emitted from the specimen in response to the pulse of UV light focussed onto a small area in the specimen.

A difficulty encountered in the use of flash photolysis in conjunction with a confocal microscope is the problem of precisely predetermining the position on a specimen at which the pulse of excitation light will be focussed. To change the target position for the excitation light from one position to another on the specimen within the field of view of the confocal microscope, the specimen slide may be moved by the operator to a position at which the excitation light will be focussed on the new target position. However, moving the specimen is generally not desirable for stability reasons. The microscope and/or flash photolysis equipment may also be adjusted based on the operator's estimate of the target position at which the excitation light will be focussed. This estimated position may not correspond exactly to the actual position of incidence of the excitation light on the specimen. In addition, typical microscope objective lenses have a somewhat different index of refraction for the UV light used for flash photolysis excitation than for visible light wavelengths, so that the actual position of incidence as estimated utilizing visible light scanning may not exactly correspond to the position at which the UV excitation light will be focussed by the objective.

SUMMARY OF THE INVENTION

The present invention allows the performance of flash photolysis operations while maintaining continuous and superimposed imaging of the target area to which the flash is directed as well as its surroundings. The invention may be readily interfaced to laser scanning imaging systems, allowing three-dimensional localization of the flash-photolysized areas and visualization of the effects of the photolysis. The present invention may also be utilized with full image microscope systems to allow continuous imaging of the targeted area during targeting, application of the flash excitation beam, and subsequent emissions from the target. In either case, continuous live imaging of the entire area under inspection is enabled with minimal modification of existing scanning imaging systems or whole field imaging systems.

Apparatus in accordance with the invention for use with scanning imaging systems includes an excitation optical coupler that receives the flash excitation beam from a suitable source, such as a UV laser, and directs that light onto an optical path through an aperture spatial filter to a main optical coupler. The main optical coupler directs the excitation beam to an optical imaging system, such as a microscope, which focusses the beam onto the desired position within a specimen. The main optical coupler is also positioned to receive a scanning beam from a scanning system, such as a confocal laser scanning system, and direct that light to the optical imaging system, and to pass light that has been reflected from the specimen back through the optical imaging system to the scanning system. The main coupler also directs some of the light from the scanning beam that is reflected from the specimen back through the aperture spatial filter to the excitation optical coupler which directs this reflected light to a target detector. The output signal from that photodetector is correlated with the output signal from the scanning system so that the scanned image displayed on a display device shows the position of the scanning beam when the reflected light from the scanning beam passes through the aperture filter, such as by summing the output signals from the scanning system detector and the target detector to provide an output signal that, when displayed on a display screen, has a greater intensity at the position of the target. When flash photolysis is to be carried out, the flash source is activated to provide the excitation beam through the excitation coupler and the aperture filter to the main coupler, where that beam is directed through the microscope to be focussed upon the position in the specimen which has been identified as the target position. Light emanated from the specimen in response to the flash photolysis excitation, i.e., fluorescence, is directed back through the microscope and through the main coupler to the scanning system where it is detected and stored and/or displayed in a conventional manner for such scanning systems.

The present invention may also be utilized in full image microscope systems, for example, where a video camera is utilized with a microscope to provide a video display of the full image from the microscope. The main coupler is connected between the camera and the microscope. A target illumination light source is connected to the excitation optical coupler in addition to the pulse excitation source. The target illumination light source provides light through the excitation optical coupler onto the optical path and through the aperture filter to the main optical coupler, where this illumination light is directed through the microscope to be focussed upon a position in the specimen. The target illumination light reflected from the specimen is passed back through the microscope and the main optical coupler to the camera, which detects the target spot as an area of brighter illumination. The output of the camera may be displayed on a video screen to show both the specimen and the more brightly illuminated target spot. When flash photolysis is to be carried out, the excitation source is activated to provide the excitation beam to the excitation optical coupler, which directs the excitation beam on the optical path through the aperture to the main optical coupler. The main optical coupler directs the excitation beam to and through the microscope to be focussed onto the same position in the specimen at which the target illumination light was focussed. The response of the specimen to the excitation beam is then captured by the camera while the camera is also imaging the full specimen, allowing the response to the flash photolysis excitation to be displayed simultaneously with the full image of the specimen.

The main optical coupler between the scanning system and the microscope may further include a reflector system that intercepts a portion of the scanning beam and reflects the intercepted portion of the scanning beam directly toward the aperture filter, in addition to or as an alternative to the scanning beam light that is reflected back from the specimen through the microscope. The use of such a reflector system enhances the intensity of the signal received by the target detector. The main coupler may include a dichroic mirror oriented obliquely to the scanning beam direction to partially transmit and partially reflect the scanning beam. The partially reflected portion of the scanning beam is directed to a lens to a retroreflector mirror which reflects it back to the lens and the dichroic mirror, functioning as a beam splitter, to be passed therethrough toward the aperture. The reflector system serves to form a conjugate image plane and relays the reflection back to the spatial aperture and to match the pupil planes, i.e., the size of the rastered area. The illumination beam from the scanning system tracks in a raster scan pattern, with the aperture positioned so that light from the illumination beam will pass through the aperture when the scanned beam passes over the aperture; this is the same position in the raster scan pattern at which the excitation beam will pass through the aperture in the opposite direction toward the dichroic mirror where it is reflected into the microscope and thus onto the specimen. The dichroic mirror in the main coupler thus acts as both a beam splitter for the illumination light provided from the scanning unit, preferably substantially passing most of the light at the illumination light wavelength, and as a dichroic mirror to substantially reflect light at the (typically shorter) wavelength of the excitation beam.

The optical path between the excitation coupler and the main coupler preferably includes a fiber optic cable to direct both the reflected illumination beam to the target detector and to direct the excitation beam to the main coupler. The optical path may further include a reflecting mirror mounted at a conjugate pupil plane for adjustment in orthogonal directions to allow precise positioning of the excitation beam and the reflected light beams with respect to the main coupler and/or with respect to the aperture. In this manner, the target position on the specimen may be adjusted by the operator without moving the specimen itself. Where the invention is utilized with a full image microscope and camera, the optical fiber may be utilized to transmit both the excitation beam and the visible light target illumination beam from the excitation optical coupler to the main optical coupler.

Further objects, features and advantages of the invention will be apparent from the following detailed description when taken in conjunction with the accompanying drawings.

DETAILED DESCRIPTION OF THE INVENTION

Figure 1:
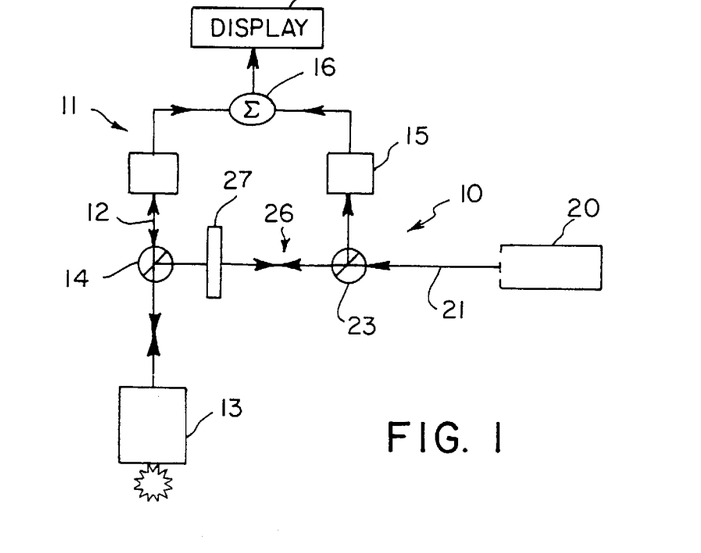
FIG. 1 is a schematic block diagram illustrating the principles of the present invention.

With reference to the drawings, flash photolysis apparatus in accordance with the invention is shown generally at 10 in FIG. 1. The apparatus 10 is adapted for use with a scanning system 11, such as a confocal microscope laser scanning system, which provides a raster scanned illumination beam 12 that is transmitted to a microscope 13 that focusses the scanning beam onto a specimen. The scanning system 11 and the microscope 13 may be commercially available systems. An example of a suitable confocal laser scanning system is shown in U.S. Pat. No. 4,863,226 to Houpt, et al., entitled "Confocal Laser Scanning Microscope." The apparatus 10 of the present invention includes a main optical coupler 14 which receives the scanning beam 12 and passes it through to the microscope 13. A pulse illumination source 20 (e.g., a mercury flash lamp, a shuttered cw ultraviolet (UV) laser, or a pulsed laser) provides an excitation beam 21 of pulses of light at selected times that will provide photolysis in the sample. The excitation beam 21 is passed to an excitation optical coupler 23. The optical coupler 23 receives the excitation beam 21 from the source and diverts the excitation beam to an optical path 26 through an aperture spatial filter 27 to the main coupler 14. When the excitation beam is not present, the main coupler 14 transmits the scanning illumination beam 12 to the microscope 13 and returns reflected (and fluorescence) light from the microscope to the scanning system 11 so that reflected light and fluorescence light images of the specimen may be obtained in the normal manner. When the pulse source 20 is activated, the main coupler 14 directs the excitation beam 21, passed through the aperture spatial filter 27, to the microscope 13 where it is focussed onto the specimen. The light emanated from the specimen in response to the excitation beam is transmitted from the microscope through the main coupler 14 to the scanning system 11, where it is detected along with reflected and fluorescence light from the rest of the specimen within the field of view of the microscope. The scanning system 11 has an internal photodetector (not shown in FIG. 1) that provides an output signal corresponding to the detected image; that signal is passed to a summing junction 16 and then to a display device 18, e.g., a video display terminal. The display device 18 will thus simultaneously display the entire image of the specimen as well as the light emanating from the target spot in the specimen at which the excitation beam was incident. When the pulse source 20 is not activated and the excitation beam is not directed to the specimen, the main coupler 14 directs a portion of the scanning beam (e.g., from the scanning beam light reflected from the specimen) toward the aperture spatial filter 27. The position of the scanning beam at which the scanning beam passes through the aperture 27 corresponds to the position on the specimen at which the excitation beam will be incident on the specimen. The scanning beam light passed through the aperture spatial filter is transmitted back on the optical path 26 to the excitation coupler 23 and is directed by it to a target detector 15. The output signal from the target detector 15 may be added at the summing junction 16 with the output signal from the scanning system 11 and the summed signal supplied to the display device 18. Since the signal from the scanning system 11 corresponds to a raster scan across the microscope field, the point in time at which the detector 15 will provide an output signal corresponds to the time at which the scanning beam is at the target position. The summed signal from the scanner 16 will thus result in a greater intensity output signal at this time and a bright spot on the video display screen at the target position on the specimen.

Figure 2:
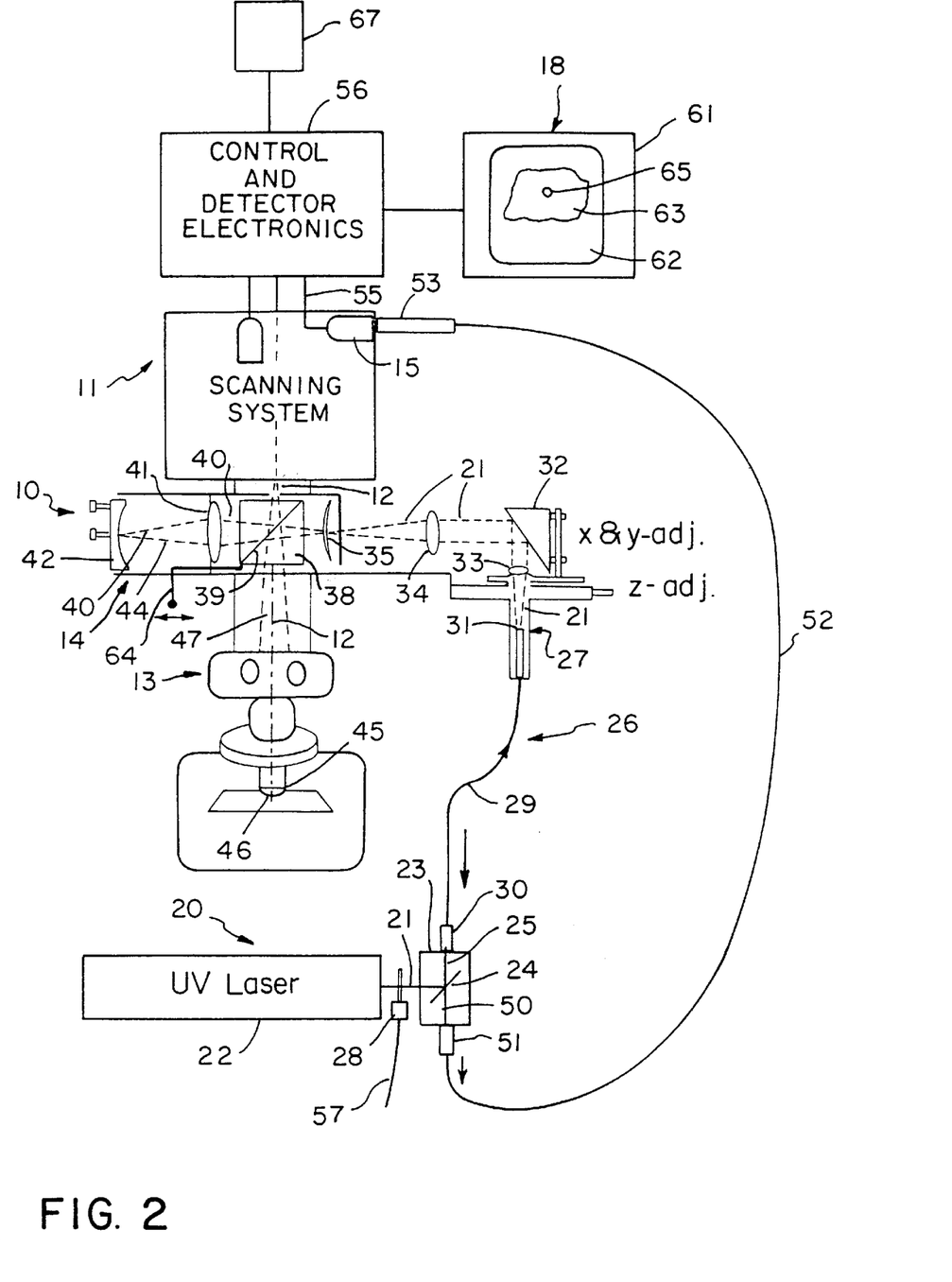
FIG. 2 is a schematic view of the flash photolysis apparatus of the present invention incorporated with a laser scanning system and an optical microscope.

An example of the implementation of the flash photolysis apparatus 10 in conjunction with a conventional confocal laser scanning system 11 is shown in FIG. 2. For exemplification, the flash excitation source 20 may comprise a cw ultraviolet laser 22 and a selectively openable pulsating shutter 28. The shutter 28 is normally closed to block the laser beam. When flash photolysis is to be carried out, the operator controls the shutter 28 to open at selected times to provide an excitation beam 21 composed of excitation light pulses of a selected pulse width (e.g., 1 to 2 m sec.) and spacing (e.g., 1 sec.). The excitation coupler 23 may be implemented in various conventional ways to provide the coupling of the reflected scanning beam and the excitation beam. For example, the coupler 23 may include a dichroic mirror 24 which reflects the short wavelength(s) of the excitation beam (e.g., at 337 nm for a nitrogen pulsed laser or the 351 nm cw line from an argon laser in conjunction with a pulsating shutter 28), while transmitting the longer wavelengths of the reflected scanning beam.

The excitation coupler 23 may be mounted directly adjacent to the main coupler 14 so that the optical transmission element forming the optical path 26 may comprise only the air space between the excitation coupler 23, the aperture spatial filter 27, and the main coupler 14. For convenience and adjustability, the optical elements in the optical path 26 shown in FIG. 2 include a flexible fiber optic coupling cable 29 (e.g., a multimode UV optical fiber) with an input coupler 30 which receives the excitation beam 21 deflected along a path 25 by the dichroic mirror 24. The excitation beam 21 exits from the cable 29 at an exit coupler 31 which has an exit end that serves as the spatial filter aperture 27. The excitation beam 21 is then collimated by a lens 33 and directed to a mirror 32 which reflects the beam to a lens 34 and a field lens 35. The 45° angle mirror 32 is preferably mounted on slides for displacement in three orthogonal (x, y, and z) directions, preferably with precision adjustment mechanisms, e.g., micrometer type threaded screws. The field lens 35 matches the pupil of the flash photolysis system to that of the microscope 13 so that the size of the rastered area on the sample is the same as that at the end 31 of the fiber cable 29. The lenses 33, 34 and 35 form a pupil plane at the mirror 32. All of the beams in the raster pass at the center of this plane. The beam 21 passes through the field lens 35 into the main channel coupler 14 and is received by a dichroic mirror beam splitter which includes a mirror face 39 oriented obliquely, preferably at a 45° angle, to the incoming beams 12 and 21. The mirror face 39 is preferably formed to reflect substantially all of the wavelengths of light in the excitation beam 21 (e.g., at UV wavelengths) and to partially reflect and partially transmit the light at the (typically longer) wavelengths of the scanning beam 12. The portion of the beam 12 that is reflected by the mirror 39, as indicated by the beam labeled 40 in FIG. 2, is focussed by a lens 41 onto a retroreflector mirror 42—preferably concave as shown—which reflects back a beam 44 to the lens 41. The reflector system forms a second conjugate image plane and relays the reflection back to the spatial filter aperture and matches the pupil planes (the size of the rastered area). The beam 44, constituting a reflected portion of the scanning beam, is received by the lens 34 and directed, as a collimated beam, to the mirror 32 where it is reflected to pass through the lens 33, which focusses the beam onto the aperture 27 at the output end 31 of the optical cable 29. Similarly, that portion of the scanning beam 12 which passes through the beam splitting mirror face 39 and is received by the microscope 13 is focussed by the objective lens 45 of the microscope onto a spot on the specimen 46. The light reflected from the specimen is passed back up through the objective 45 of the microscope to form a converging reflected beam 47, a part of which passes through the mirror face 39 into the scanning system 11 to be detected in a conventional manner. A part of the reflected beam is also reflected by the beam splitting mirror face 39 to be brought to focus at the plane of the aperture 27. When the scanning beam light reflected by the mirror 39 reaches a position in which it passes through the aperture 27, it is then directed by the optical elements in the optical path 26 back to the excitation coupler 23, adding to the light that was directed back on the path 26 by the retroreflecting mirror 42. The combined reflected light exits from the optical fiber cable 29 along the path 25 and passes through the dichroic mirror 24, which is formed to substantially transmit the longer wavelengths of the scanning beam. The light transmitted through the dichroic mirror 24 is indicated by the line 50 in FIG. 2. The light transmitted along the line labeled 50 is received at an entrance end 51 of an optical fiber cable 52. The cable 52 directs the light to the exit end 53 of the cable where the light is received by a target detector 15, e.g., a photomultiplier tube. The detector 15 provides an output signal on a line 55 to the control and detector electronics 56, which are conventional electronics associated with the scanning system 11 (e.g., a Noran Instruments, Inc. Oz™ confocal laser scanning system). The control and detector electronics 56 also provides a signal on a line 57 to the pulsating shutter 22 to control its opening and closing and thus the passage of the excitation beam 21.

The shutter 22 is initially closed (or the laser 20 inactivated where a pulsating laser is utilized as a source) when the scanning system 11 is to be operated in a normal manner without flash photolysis experiments. The scanning beam 12 from the scanning system traces out a raster scan pattern over the specimen 46. The reflected light from the specimen that is directed back through the optics of the microscope 13 is received by the scanning system 11 and is detected to provide an output signal proportional to the detected light intensity, and the output signal is correlated with the position of the scanning beam to allow a visual image of the specimen to be displayed on a display unit 18, such as a video display terminal 61, which has a video screen 62 on which a portion 63 of the specimen is displayed. The light from the scanning beam that is reflected from the retroreflector 42 and that passes through the mirror face 39, and the light from the specimen that is reflected by the beam splitting mirror 39 back on the optical path 26 toward the aperture 27, add together and also follow a raster scan pattern as this light is incident upon the plane of the aperture 27. The retroreflector 42 may be mounted on a sliding support 64 to allow the position of the retroreflector to be adjusted so that the light from the retroreflector is focussed on the plane of the aperture 27. The aperture 27 is located at a position within the raster scanned pattern that is projected onto the aperture plane. Thus, light passes through the aperture 27 only when the scanning beam passes over the open aperture 27. At this time, a pulse of light passes back through the optical elements on the optical path 26 to the excitation channel coupler 23 and thence on the optical cable 52 to the target detector 15. The output signal provided on the line 55 to the control and detector electronics 56 is correlated by the detector electronics with the position of the scanning beam at the time that the signal is received on the line 55, thus allowing the control and detector electronics to determine the position in the raster scan pattern at which the beam is passed through the aperture 35. This position may be displayed on the video display by a marker, e.g., a brighter spot, as illustrated at 65 in FIG. 2.

When the user decides to do flash photolysis and provides an instruction signal to the control and detector electronics 56 to that effect from an interface unit 67, the control electronics 56 provides a signal on the line 57 to open the pulsating shutter 22 at selected times to allow pulses of light in the excitation beam 21 to pass through for selected pulse durations. The excitation beam pulses are then reflected by the dichroic mirror 24 onto the optical path 26 and pass through the aperture 27. The excitation beam light pulses are then reflected by the dichroic mirror face 39 into the microscope 13, where they are focussed by the objective lens 45 onto the specimen 46. Because the excitation beam passes through the same aperture 27 as the reflected scanning beam light when the scanning beam reached the point in the raster pattern at which it passes over the aperture 27, the excitation beam light will be focussed onto the same position 65 in the sample as was indicated by the detected scanning beam light. If the objective lens and other lenses in the microscope 13 have a different index of refraction for ultraviolet light than for visible light, a predictable displacement of the actual position of incidence of the ultraviolet excitation light will occur. Because the displacement is predictable, the control and detector electronics 56 may be programmed to provide an appropriate correction so that the position 65 displayed on the video screen 62 is, in fact, the position at which the excitation beam pulses will be focussed.

The excitation beam pulses stimulate photolysis in the specimen and the emanation of fluorescent light from the specimen. This fluorescent light, at a longer wavelength than the excitation light, passes back through the microscope objective lens 45 (and other typical lenses of the microscope) to the dichroic mirror beam splitter face 39, through which it passes to be detected in the scanning system 11. If desired, the fluorescent light may also be partially reflected by the beam splitter face 39 to and through the optical path 26 to the coupler 23, where it passes through the dichroic mirror 24 since its wavelength is longer than that of the excitation beam 21. This fluorescent light is then received by the optical cable 52 and directed by it to the detector 15 to provide an output signal 55 to the control and detector electronics that is proportional to the intensity of the fluorescence signal. In this manner, the intensity of the flash photolysis fluorescence at the precise position 65 in the sample may be determined.

To change the position of the target in the specimen, the user may operate x, y and z position adjusters for the mirror 32 until the brighter target spot appears at the right position on the screen 62. The mirror 32 may also be replaced by a reflective diffuser to allow adjustment of the target spot size. Lenses 33, 34 and 35 form a pupil plane at the mirror 32. All of the beams in the raster pass at the center of this plane. Therefore, tilting the mirror 32 at this plane results in a change of the direction of the excitation beam and at the same time causes the fiber aperture 27 to see the rastered beam coming at the same direction. The result is that the target spot will be seen to move across the field of view and the excitation beam will also be directed at that new spot position. For the same reasons, placing a reflective diffuser at that pupil plane diffuses the excitation light into a cone of angular directions, causing the light focussed onto the specimen to spread out, thereby changing the spot size of the excitation. At the same time, because of this diffuser, the fiber aperture will "see" rastered laser coming from a wider angle range and the displayed target signal will be larger. From optical symmetry principles, the displayed target is of the same size (and shape) as that of the focussed excitation light on the sample. Thus, the tiltable diffusing mirror 32 allows positioning of the spot center anywhere in the sample without loss of brightness at the end of the field of view, and permits increasing the size of the spot by switching (using a linear slider or a wheel) to another reflector having a more diffusing reflective surface.

Figure 3:
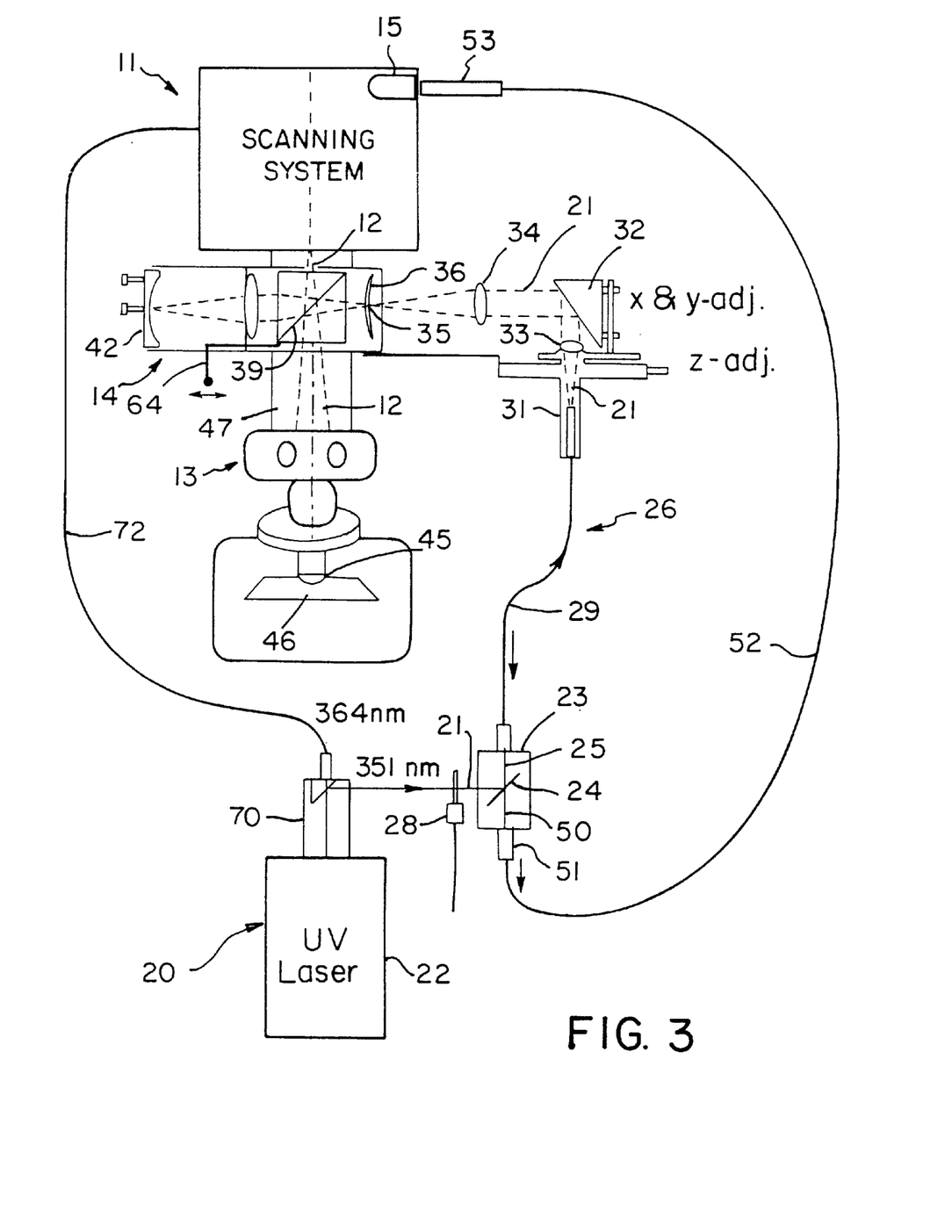
FIG. 3 is a schematic view of a modified embodiment of the apparatus of FIG. 2.

The apparatus of the invention may be modified as shown, for example, in FIG. 3, to allow the source 20 to be used also to provide the scanning beam for the scanning system 11 where the system is to be used for fluorescence imaging. For example, the source 20 may be a UV laser having multiple output lines including, e.g., the 351 nm line and the 364 nm line. A wavelength selector 70 (e.g., spectrometer prisms or diffraction gratings) is mounted to receive the multi-line output of the laser 20 and to separate the laser lines, directing the beam 21 (e.g., at 351 nm) to the pulsating shutter 28 and thence to the rest of the apparatus 10 to be used in the same manner as described and illustrated above with respect to FIG. 1. The wavelength selector device 70 also passes another of the laser lines (e.g., the 364 nm line) to the input end 71 of an optical fiber cable 72 which directs the laser light to the scanning system 11 where it may be utilized in a normal manner when the scanning system is used to do epifluorescence imaging. When such imaging is being carried out, the shutter 28 is closed so that the excitation beam 21 is not directed through the system to the sample. When flash photolysis experiments are to be carried out, the scanning system 11 may utilize the light transmitted on the fiber cable 72 or may utilize another source for general illumination light, and the light on the beam 21 is applied to the specimen by operating the pulsating shutter in the manner described above.

Figure 4:
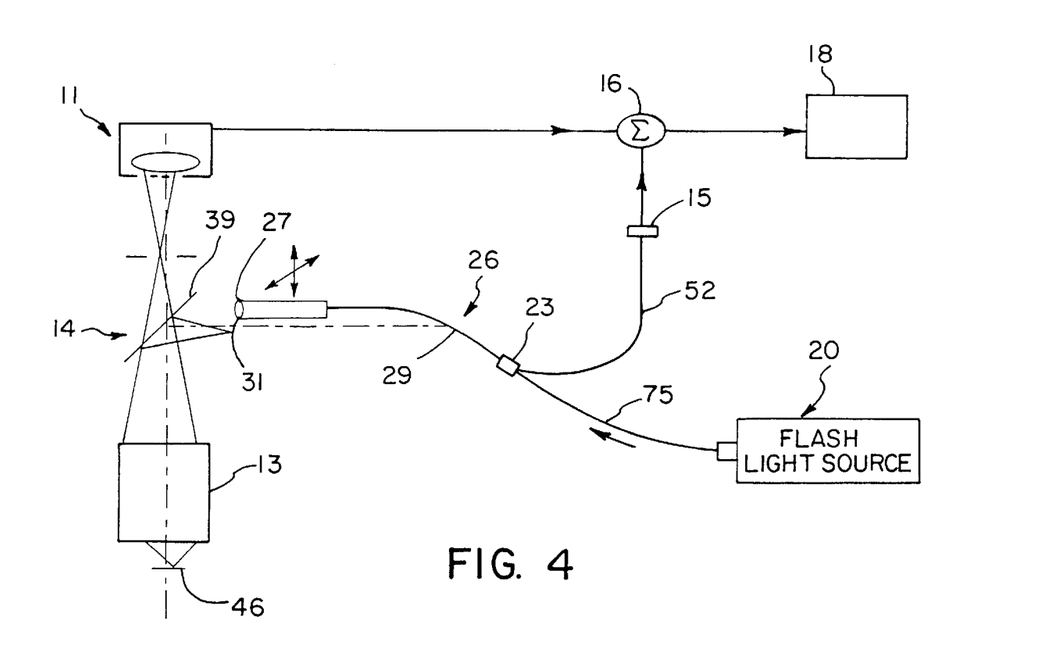
FIG. 4 is a simplified schematic view of the apparatus of the invention utilizing fiber optic cables for the entire optical path between the flash excitation source and the main optical coupler and between the main optical coupler and the target detector.

As illustrated in FIG. 4, the present invention may be implemented utilizing optical fibers for the entire optical path from the excitation beam source 20 to the main coupler 14. The excitation coupler 23 may comprise a bidirectional fiber optic coupler of standard design, with the excitation beam from the source 20 directed to the coupler 23 by a fiber optic cable 75. The exit end 31 of the cable 29 may be utilized as the spatial filter aperture 27 and, if desired, the exit end 31 of the cable may be mounted to be adjusted in position to adjust the position of the target position on the specimen.

Figure 5:
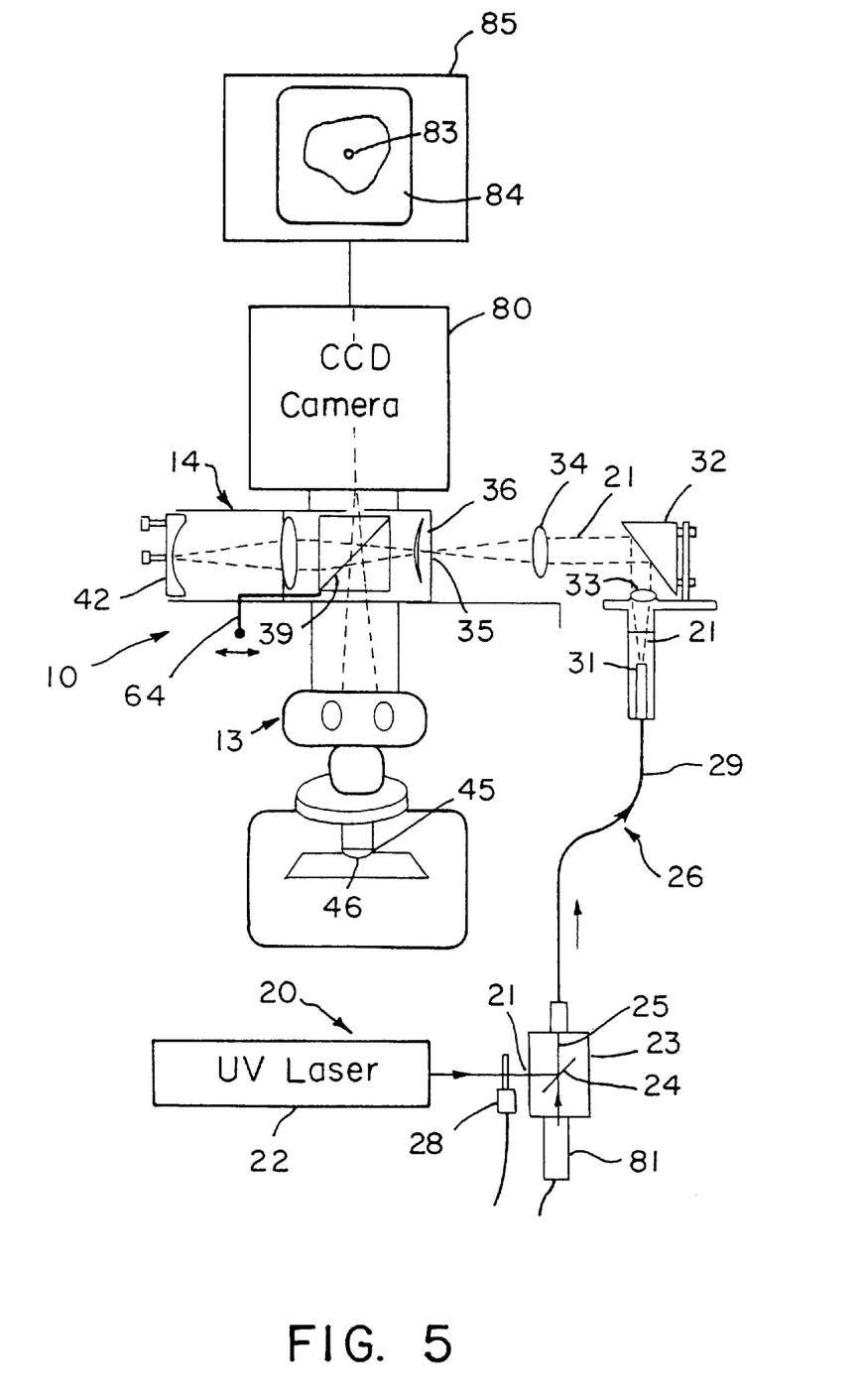
FIG. 5 is a further embodiment of the present invention incorporated in a microscope system utilizing a full image camera.

The present invention may also be utilized with full image capture microscope systems as well as scanning systems. An illustration of the application of the apparatus 10 of the invention with respect to a full image microscope system is shown in FIG. 5, in which a full image detector 80, e.g., a charge coupled device (CCD) camera, is mounted to receive the light from the microscope 13 that has either been projected upon and reflected from the specimen, or transmitted through the specimen, in conventional full image illumination. For this application, a visible light target illumination source 81, e.g., a light emitting diode, is connected to the coupler 23 in place of the optical cable 52 of FIG. 2, to provide a visible light input signal that travels through the coupler 23 into the optical cable 29 along the same optical path 26 as would be followed by the excitation beam from the excitation source 20. The light from the target illumination source 81 is directed by the main coupler 14 into the microscope 13, which focusses the visible light onto the target position in the specimen. The light reflected from the specimen is directed back through the microscope 13 and through the coupler to the camera 80, showing up as a bright spot 83 on the screen 84 of a video display terminal 85. Since the light from the source 81 is focussed onto the same target position in the specimen 46 as will be the excitation beam from the excitation source 20, the operator thus knows exactly where flash photolysis will occur in the specimen under observation. To carry out flash photolysis, the light source 81 is then turned off and the pulsating shutter 28 operated to send the pulsed excitation beam 21 through the optical system and to the specimen, and the fluorescent light emanated from the specimen may be detected by the camera 80 and displayed on the video screen 84.

It is understood that the invention is not confined to the particular embodiments set forth herein as illustrative, but embraces all such modified forms thereof as come within the scope of the following claims.

What is claimed is:

1. Flash photolysis apparatus for use with a microscope and a scanning system that produces a scanning beam for illumination of a specimen, comprising:

(a) a pulse illumination source providing an excitation beam of pulses of light of a selected wavelength at selectable times that can provide photolysis;

(b) an excitation coupler receiving the excitation beam from the source and directing the excitation beam on a path, the excitation coupler passing light therethrough at wavelengths longer than the wavelength of the excitation beam received from the path on which the excitation beam is directed;

(c) a main coupler including a dichroic mirror beam splitter;

(d) optical transmission elements forming an optical path directing the excitation beam from the excitation coupler to the dichroic mirror beam splitter, the dichroic mirror beam splitter directing the excitation beam on a path wherein the beam may be focussed by the optics of a microscope onto a specimen, the dichroic mirror beam splitter also accepting a scanning beam from a scanning system and passing a portion of the scanning beam therethrough so that it may be directed to the microscope, the dichroic mirror beam splitter also directing a portion of the scanning beam back on the optical path to the excitation coupler through an aperture that is positioned so that the portion of the scanning beam so directed passes through the aperture into the optical path when the scanning beam passes over the aperture; and (e) a target detector receiving the portion of the scanning beam from the optical path that passes through the aperture, the detector providing an output signal when it receives the scanning beam light, whereby the detector output signal may be correlated with the scanning beam to determine the relative position in the specimen at which the scanning beam passes through the aperture and thereby the position on the specimen at which a pulse of light in the excitation beam from the pulse illumination source will be incident.

2. The-apparatus of claim 1 wherein the main coupler includes a retroreflecting mirror and wherein the dichroic mirror beam splitter is positioned to receive and reflect the excitation beam from the source to the microscope to be focussed onto the sample, is positioned to partially transmit the scanning beam through the dichroic mirror beam splitter into the microscope to be focussed onto the sample, and is positioned to partially reflect a portion of the scanning beam to the retroreflecting mirror which is positioned to reflect the scanning beam back to the dichroic mirror beam splitter to partially pass therethrough and thence through the aperture onto the optical path to the excitation optical coupler and thence to the target detector.

3. The apparatus of claim 1 wherein the pulse illumination source comprises a laser providing a continuous output beam and a pulsating shutter intercepting the output beam from the laser and selectively passing pulses of light therethrough.

4. The apparatus of claim 1 wherein the optical path includes a fiber optic cable.

5. The apparatus of claim 4 wherein the fiber optic cable extends from the excitation optical coupler to a position where it receives a reflected scanning beam light passed through an aperture at the exit end of the fiber optic cable.

6. The apparatus of claim 5 further including a second fiber optic cable extending from the excitation optical coupler to the target detector and positioned to receive the scanning beam light passed through the aperture and transmitted on the fiber optic cable to the excitation optical coupler, and to transmit that light to the target detector.

7. The apparatus of claim 2 wherein the retroreflecting mirror is a concave mirror and including a lens between the dichroic mirror beam splitter and the concave retroreflecting mirror to focus the light from the dichroic mirror beam splitter passed through the lens onto the retromirror and to focus reflected light received from the retromirror that is passed through the dichroic mirror beam splitter onto the aperture.

8. The apparatus of claim 1 wherein the pulse illumination source comprises a pulsed laser that provides output pulses of light at selectable times.

9. The apparatus of claim 1 wherein the optical path includes a mirror with a reflecting face receiving the excitation beam and reflecting the beam onto a path to the dichroic mirror beam splitter, the mirror mounted for adjustment of the position of the face of the mirror to allow adjustment of the position at which the excitation beam is incident upon a specimen.

10. Flash photolysis apparatus for use with a microscope and a scanning system that provides a scanning illumination beam, comprising:

(a) a pulse illumination source providing an excitation beam of pulses of light at a selected wavelength at selected times that can provide photolysis;

(b) a target detector that provides an output signal when it receives illumination light that is related to the intensity of the light;

(c) excitation optical coupling means for receiving the excitation beam from the source and directing the excitation beam on an optical path and for receiving light on the same optical path at a different wavelength than the excitation beam and passing that light on a path to the target detector; and (d) main optical coupling means adapted to be mounted between a scanning system and a microscope for receiving the scanning beam from the scanning system and passing that scanning beam to a microscope, for receiving reflected light from the microscope and directing that reflected light to the scanning system, for receiving the excitation beam from the excitation optical coupling means that is passed along the optical path and directing that excitation beam to the microscope, for receiving fluorescence light from the microscope emitted in response to the excitation beam and directing the emitted light to the scanning system, and for directing a reflected portion of the scanning beam toward an aperture that is aligned with the optical path to the excitation optical coupling means such that the scanning beam passes over the aperture to provide light that passes along the optical path to and through the excitation coupling means to the detector when the scanning beam is at the position at which the excitation beam from the source that is passed along the optical path through the aperture will be directed by the main optical coupling means to the microscope and focussed on a specimen.

11. The apparatus of claim 10 wherein the excitation optical coupling means comprises a dichroic mirror that receives the excitation beam from the source and reflects the excitation beam while being formed to pass light at selected wavelengths lower than the wavelength of the excitation beam.

12. The apparatus of claim 10 wherein the optical path between the excitation optical coupling means and the main optical coupling means includes a fiber optic cable and wherein the excitation optical coupling means includes a fiber optic bidirectional coupler.

13. The apparatus of claim 10 wherein the main optical coupling means includes a dichroic mirror beam splitter which is positioned to receive and reflect the excitation beam from the source to the microscope to be focussed onto the specimen, is positioned to partially transmit the scanning beam through the dichroic mirror beam splitter into the microscope to be focussed onto the specimen, and is positioned to partially reflect a portion of the scanning beam to a retroreflecting mirror which reflects the scanning beam back to the dichroic mirror beam splitter to partially pass therethrough and thence through the aperture onto the optical path to the excitation optical coupling means and thence to the detector.

14. The apparatus of claim 13 wherein the retroreflecting mirror has a concave surface and further including a focussing mirror between the retroreflecting mirror and the dichroic mirror beam splitter.

15. The apparatus of claim 10 wherein the optical path includes a fiber optic cable.

16. The apparatus of claim 15 wherein the fiber optic cable extends from the excitation optical coupling means to a position where it receives light passed through an aperture at the exit end of the fiber optic cable.

17. The apparatus of claim 16 further including a second fiber optic cable extending from the excitation optical coupling means to the target detector and positioned to receive the scanning light beam passed through the aperture and transmitted on the fiber optic cable to the excitation coupling means, and to transmit that light to the detector.

18. The apparatus of claim 10 wherein the pulse illumination source comprises a laser providing a continuous output beam and a pulsating shutter intercepting the output beam from the laser and selectively passing pulses of light therethrough.

19. The apparatus of claim 10 wherein the pulse illumination source comprises a pulsed laser that provides output pulses of light at selectable times.

20. The apparatus of claim 10 wherein the optical path includes a mirror receiving the excitation beam and reflecting the beam onto a path to the main optical coupling means, the mirror mounted for adjustment of the position of the face of the mirror to allow adjustment of the position at which the excitation beam is incident upon a specimen.

21. Flash photolysis apparatus for use with a microscope and an image capture system that provides a full image display of the microscope image, comprising:

(a) a pulse illumination source providing an excitation beam of pulses of light at a selected wavelength at selected times that can provide photolysis;

(b) a target light source that provides a target illumination beam of target illumination light;

(c) excitation optical coupling means for receiving the excitation beam from the pulse illumination source and the target illumination beam from the target illumination source and for directing the excitation beam and target illumination beam on the same optical path;

(d) main optical coupling means, adapted to be mounted between an image capture system and a microscope, for receiving light from the microscope and directing that light to the image capture system, for receiving the excitation beam from the excitation optical coupling means that is passed along the optical path and directing that excitation beam to the microscope, for receiving the target illumination beam from the optical path and directing that target illumination beam to the microscope, and for receiving fluorescence light from the microscope emitted in response to the excitation beam and directing the emitted light to the image capture system.

22. The apparatus of claim 21 wherein the excitation optical coupling means comprises a dichroic mirror that receives the excitation beam from the source and reflects the excitation beam while being formed to pass the target illumination beam light at wavelengths lower than the wavelength of the excitation beam.

23. The apparatus of claim 21 wherein the optical path between the excitation optical coupling means and the main optical coupling means includes a fiber optic cable and wherein the excitation optical coupling means includes a fiber optic bidirectional coupler.

24. The apparatus of claim 21 wherein the main optical coupling means includes a dichroic mirror beam splitter which is positioned to receive and reflect the excitation beam and the target illumination beam to the microscope to be focussed onto a specimen.

25. The apparatus of claim 21 wherein the optical path includes a fiber optic cable.

26. The apparatus of claim 21 wherein the pulse illumination source comprises a laser providing a continuous output beam and a pulsating shutter intercepting the output beam from the laser and selectively passing pulses of light therethrough.

27. The apparatus of claim 21 wherein the pulse illumination source comprises a pulsed laser that provides output pulses of light at selectable times.

28. The apparatus of claim 21 wherein the optical path includes a mirror receiving the excitation beam and the target illumination beam and reflecting the beams onto a path to the main optical coupling means, the mirror mounted for adjustment of the position of the face of the mirror to allow adjustment of the position at which the excitation beam and target illumination beams are incident upon a specimen.

29. A method of carrying out flash photolysis with a microscope and a scanning system that provides a scanning illumination beam to the microscope, comprising the steps of:

(a) directing the scanning illumination beam in a raster pattern into the microscope to be focussed on a specimen and detecting the reflected light from the specimen passed back to the scanning system and displaying the detected image of the specimen;

(b) deflecting scanning beam light toward an aperture such that the scanning beam light passes through the aperture at a selected position in the raster scanning pattern of the scanning beam;

(c) detecting the scanning beam light passed through the aperture and displaying the position in the image of the specimen at which the scanning beam passed through the aperture;

(d) when flash photolysis is to be carried out then passing an excitation beam of pulses of light at a selected wavelength that can provide photolysis through the aperture along the same path as the scanning beam light that passes through the aperture and is detected, and directing the excitation beam passed through the aperture into the microscope and focussing it on the specimen.

30. The method of claim 29 including the step of detecting fluorescence emissions from the specimen in response to the excitation beam and displaying the image of the detected fluorescence superimposed on the displayed image of the specimen obtained from the reflected scanning beam.

31. The method of claim 29 wherein the step of deflecting the light from the scanning beam toward an aperture is carried out with a beam splitter in the path of the scanning beam that passes the scanning beam to the microscope and partially reflects scanning beam light reflected from the specimen toward the aperture.

32. The method of claim 29 wherein the step of deflecting light from the scanning beam toward an aperture is carried out by partially reflecting the scanning beam by a beam splitter to a retroreflecting mirror to reflect the light back through the beam splitter toward the aperture.

33. The method of claim 29 in which the excitation beam is composed of pulses of light at ultraviolet wavelengths.

34. The method of claim 29 wherein the step of detecting the scanning beam light is carried out by directing the light passed through the aperture along an optical path at least part of which is provided by an optical fiber.

35. A method of carrying out flash photolysis with a microscope and an image capture system that provides a full image display of the microscope image, comprising the steps of:

(a) detecting reflected light from a specimen passed from a microscope to the image capture system and displaying the detected image of the specimen;

(b) directing a target illumination beam of light along an optical path into the microscope to be focussed on a selected position in the specimen; and (c) when photolysis excitation is to be carried out passing an excitation beam of pulses of light at a selected wavelength at selected times that can provide photolysis into the microscope along the same optical path as the target illumination beam and focussing the excitation beam onto a position in the specimen corresponding to the target position.

36. The method of claim 35 including the step of detecting fluorescence emissions from the specimen in response to the excitation beam and displaying the image of the detected fluorescent superimposed on the displayed image of the specimen.

37. The method of claim 35 in which the excitation beam is composed of pulses of light at ultraviolet wavelengths.

* * * * *